United States Patent [19]

Silvestrini

[11] Patent Number: 4,960,709

[45] Date of Patent: Oct. 2, 1990

[54] KIT FOR USE IN THE DETERMINATION OF THE PROLIFERATIVE ACTIVITY IN HUMAN TUMOURS

[75] Inventor: Rosella Silvestrini, Milan, Italy

[73] Assignee: Istituto Nazionale Per Lo Studio E La Cura Dei Tumori, Milan, Italy

[21] Appl. No.: 8,260

[22] Filed: Jan. 29, 1987

[30] Foreign Application Priority Data

Jan. 31, 1986 [IT] Italy .................. 19249 A/86

[51] Int. Cl.$^5$ .............................. G01N 33/48
[52] U.S. Cl. ....................... 436/64; 436/59; 435/240.2; 435/810; 435/240.25
[58] Field of Search .............. 435/810, 240, 241, 35, 435/34, 29; 436/59.64

[56] References Cited

U.S. PATENT DOCUMENTS

| | | | |
|---|---|---|---|
| 3,953,290 | 4/1976 | Uthne et al. ................... | 435/244 |
| 4,237,225 | 12/1980 | Hamill ........................... | 436/75 |
| 4,242,186 | 12/1980 | Moran et al. .................. | 436/56 |
| 4,321,058 | 3/1982 | Tomiyama et al. ............ | 436/63 |
| 4,336,333 | 6/1982 | Hamill et al. .................. | 436/75 |
| 4,629,783 | 12/1986 | Cosand ........................... | 435/5 |

OTHER PUBLICATIONS

*Tissue Culture Techniques*, Nuzzolo et al., Pub. by Warren H. Green Inc. 1983.

*Primary Examiner*—Christine M. Nucker
*Assistant Examiner*—Lyle Aleandary-Alexander
*Attorney, Agent, or Firm*—Bucknam and Archer

[57] ABSTRACT

Kit for use in the determination of the proliferative activity in human tumours, characterized mainly by a container containing, in assembled and lyophilized form, the four basic components (culture medium, antibiotic, serum and radioactive metabolic precursor) necessary to fix the tumoural material fragments rapidly and easily, without any fear of degradation and granting reliable results.

4 Claims, No Drawings

KIT FOR USE IN THE DETERMINATION OF THE PROLIFERATIVE ACTIVITY IN HUMAN TUMOURS

The present invention refers to a kit for use in the determination of the proliferative activity in human tumors. The kit has been found to have the features of simplicity and operative reproducibility.

In human oncologic pathology, as in any other pathology, the main object is to improve the therapeutic results and, if possible, to effect the recovery of the patient affected by the tumor; of course this object calls for the provision of suitable therapeutic means.

Unfortunately, apart from local surgery or radiation treatment, there do not at present exist selective therapeutic aids for the tumoral cell to be used as single treatment of the forms spread in different regions of the organism, or as adjuvant or precautional therapy whenever the local treatment has not been drastic, or where there is a high probability that tumoral cells, even if not clinically detectable, have already spread to other organs or tissues.

The lack of selectivity against tumoral cells of the presently available drugs results in toxic side effects, of minor or major importance, towards normal organs or tissues; the consequence is the need for careful use of the therapy, adjusting the intensity according to the biological aggressiveness of the tumor. In other words, the present shortage of selective therapeutic means for the tumoral cells stresses the extreme importance of using said means by rationally adjusting the level of use to the seriousness of the disease.

Unfortunately, experience shows that tumors considered similar on the grounds of their clinical characteristics may display a wide variation in their development. Also the microscopic examination of the morphological features of the tumor, carried out by an anatomical pathologist, yields exact diagnostic information, but often gives only imprecise and crude indications of the prognosis.

It is therefore expedient and important to carry out studies aimed at the discovery of biological factors or markers which lead to more and more precise prediction of the evolution and progression of the disease.

The remarkable research efforts made in the last decades in this field of oncology may be summarized as the search for:

(1) particular characteristics of different tumoral kinds, often correlated with characteristics of the tissue or organ where the tumor occurs;
(2) characteristics common to all the tumoral kinds, independently of the original organ or tissue.

The aspects considered along the first line of research include a wide and diversified spectrum of factors present in the tumoral tissue or in the biological liquids (blood, urine) of the subject bearing the tumor. By following instead the second line of research, the more obvious common denominator is represented by the remarkable proliferative activity of the tumoral cells.

In fact, even though the multiplicative capacity of the cells represents a non-exclusive feature of the tumoral tissues, which is common also to normal tissues (bone marrow, intestinal mucosa, etc.) it is reasonable to suppose that the real growth of the tumoral volume or mass is somehow related or proportional to the number of involved cells and to their proliferation rate.

In accordance with this hypothesis, since 1970 characterising studies on the proliferative activities of tumors have been made and, taking into account the considerable biological differences between tumors experimentally induced in laboratory animals and those occurring in man, the study has been directly aimed at human tumors.

Conventional methodology for the determination of the proliferative activity in human tumors The methodologies used at the beginning of the studies had considerable ethical limitations connected with the administration of radioactive substances to the patient and the need to repeatedly take tumoral tissue samples; as a consequence, their performance was limited and the extension of the study to wide and consecutive patient series was precluded.

The conviction that the study of the cellular proliferative activity could provide useful information both for scientific purposes (for a better comprehension of the tumor biology and development), and for clinical practical purposes (for a rational planning of treatment), prompted the search for simpler and more easily practical methodologic approaches.

The determination of the cellular kinetics has therefore been transferred from the "in vivo" system, i.e. from the patient, to the "in vitro" system, i.e. to the test-tube, eliminating thereby the potential hazard of radioactivity for the patient, who is no longer subjected the fatiguing procedure of multiple biopsies. The methodology which is now concordantly used by those skilled in the art, may be summarized as follows:

the tumoral tissue obtained by biopsy or during surgical operation, cut into fragments having sizes of a few mm, is incubated for 1 hr at 37° C. with stirring in a test-tube containing culture-medium, convenient nutritive factors and a radioactive substance, such as thymidine. The thymidine, commonly present in the cells, is selectively uptaken into the proliferative cells;

after 1 hour contact of the cells with the labelled metabolic precursor, the culture medium is removed the tissue fragments are treated with a fixative substance so as to ensure the morphological conservation of the tissue;

according to the usual histological procedure, the tumoral fragments are subjected to subsequent treatments in ethyl alcohol at increasing concentrations so as to make them transparent, and then incorporated into paraffin;

the tissue is cut by means of a microtome into thin sections 4 m$\mu$ thick;

the so obtained histologic sections are contacted with a photographic film (autoradiographic method). This contact is carried out in the dark and, continuously in the dark, is maintained for 8-10 days to allow the radiations from the biological sample to form photographic images sufficient in number and intensity;

the latent photographic images so formed are developed by means of usual photographic development and fixing procedures;

the so obtained samples are colored according to the usual procedures with hematoxylin and eosine;

the proliferant cells initially present in the tumor, having uptaken the labelled precursor, are able to provide autoradiographic images which may be displayed using an optical microscope.

The ratio between labelled cells and the total number 10 of cells:

$$LI = \frac{\text{No. labelled cells}}{\text{No. total cells}}$$

is named labelling index (LI).

Said ratio, hypothetically considered as an expression of the tumor proliferative rate, has already been found to be a real prognostic marker in certain kinds of solid and systemic human tumors studied up to now, such as breast and oral cavity tumors, melanomas, lymphomas and myelomas.

The above described method has the following advantages:

it uses limited amounts of tumoral cells; it does not require therefore a surgical operation but only a bioptic sampling;

it calls for only a single sampling;

it is relatively easy from the methodological point of view;

it may be easily standardized, so as to allow a significant comparison between the results obtained by different research groups;

it calls for a total time compatible with clinical needs, so that it is already used for the determination of the proliferative activity of human tumors both for scientific and clinical purposes.

There is however a limitation presently precluding the extension of such methods to all clinical environments. The limitation results from the fact that the uptake of the labelled precursor in the tumoral cells is an active phenomenon and it must therefore be carried out on vital cells and thus within a short interval (about 30 minutes) from the collection of the tumoral material.

The preparation and the performance of the first steps, preclude therefore its use in clinical institutes not endowed with suitable laboratories.

The consequence of this limitation is comprehensible if one considers that the proliferative activity is not only an aspect of the tumor biology, but it is presently considered an important potential reference element, superior to other usually used factors, for therapy planning.

The limitation may be partially overcome for those clinical institutes existing in the same town as a reference laboratory, or not far from it (even if the personnel engagement and transport needs cost more than that required by the analysis itself), but it is presently insuperable for long distances. The problem is noticed in Europe, abroad and particularly in the United States, where the distances between the different clinical institutes and the reference laboratories are often great, so as to make it necessary to use alternative methods, which will probably be more expensive and less accurate.

Methodology in accordance with the present invention

There has now been found a kit making the determination of the proliferative activity of human tumors feasible not only for patients of some privileged institutes, but of all the clinical and hospital centers, not having laboratory facilities formerly considered essential.

By means of the kit of the invention, every medical institute may carry out the first methodological steps, which need fresh and vital material.

The kit of the invention, in a preferred embodiment thereof, comprises:

(a) a vial (hermetically sealable, having a rubber plug with a threaded ring, a capsule or screw-like plug), containing in lyophilized form the culture medium, the antibiotics, the serum and the radioactive metabolic precursor; these components, according to a known procedure, having been combined immediately before use;

(b) a vial containing distilled water;

(c) a vial containing a fixative agent;

(d) a vial containing alcohol (80°);

(e) a container for waste liquids; and (f) means of the transfer of liquids.

As a culture medium in component (a), commercially available media are suitable, such as those known under the trade names RPI 1640, Mc Coy's 5A, MEM alpha, Medium 199.

As serum, fetal calf serum, bovine serum, calf serum or horse serum may be suitably used.

Finally, suitable examples of radioactive metabolic precursors comprise DNA precursor such as 3H-thymine,3H-deoxyuridine,3H-bromodeoxyuridine,14-C-thymidine, 125-iodo-deoxyuridine; RNA precursors such as 3H-uridine or protein precursors such as 3H-leucine,14-C-leucine, 35S-methiorine.

A typical composition of the component (a), given by way of an example, comprises 1.9 ml of Mc Coy's 5A medium, 0.38 ml of fetal calf serum, 190 U.I. of penicillin, 190 ug of streptomycin,, 0.1 ml of a saline solution of 3H-thymidine (12 $\mu$C, 5 C/$\mu$ mol.). Glutamine may also be added as a pH regulating agent.

As a fixative agent, a conventional Bouin solution may be suitably used.

As an example of the practical use, the tumoral material (comprising a single sample in the case of bioptic collection or 5–10 fragments having sizes of some millimeters in the case of surgical collection) is introduced into the vial (a) 1 hour after the addition to the latter of the distilled water of vial (b). After 1 hour of incubation at 37° C., the liquid is transferred, by one of the means (f), from the vial (a) to the container (e); the fixative agent is then introduced into the vial (a). After one additional hour, the fixative is also transferred into the container (e), whereas the ethanol is introduced into the vial (a).

We believe that the innovative aspect of the kit according to the invention is provided by the content of the container (a). In fact, the possibility of combining in lyophilized form the four components (culture medium, antibiotics, serum and radioactive metabolic precursor) has been never considered in the prior art, and it is surprising that the combination may be realized and that it preserves indefinitely its full functionality.

The reliability of the system according to the invention has been confirmed by tests carried out on different kinds of human tumors in short-term cultures and using different kinds of media, serums and cellular metabolic precursors labelled with tritium, radioactive carbon, iodine or cobalt ect. These tests showed that the lyophilization of all the different reagents and the subsequent reconstitution in distilled water do not change the original characteristics of the nutritive components and of the labelled substances, even if the reconstitution is carried out after many months of stockage of lyophilized product.

The initial volume of the medium, serum, antibiotics and radioactive precursors which is lyophilized and the volume of reconstitution liquid, which in a preferred embodiment are respectively 2 and 2 ml, may be extended from a 1:1 ratio to a 3:1 ratio. The advantages of the kit with respect to the prior art may be summarized as follows:

(a) a lyophilized product, easily and long-term preservable, is made available to any hospital or clinic or single physician, the lyophilized product comprising the four essential reagents: culture medium, serum, antibiotics and radioactive metabolic precursor;

(b) from the lyophilized product, the solution into which the fresh tumoral tissue is introduced is obtained in a very easy way, by simple addition of distilled water, also comprised in the kit, in a suitable amount;

(c) the tissue fragments may be histologically fixed "in situ", by means of the reagents present in the kit, avoiding any degradation risk and assuring reliability of results;

(d) there is no need for often complex procedures for buying radioactive material, serum, antibiotics and culture medium;

(e) the dilution operations of the radioactive material and the antibiotics, as well as the operations to combine the different reagents are eliminated;

(f) the tumoral material prepared and fixed may then be transferred, without any fear of degradation, to the specialized laboratories, for the completion of the analysis.

Finally, another feature of the kit, is the absolute procedure standardization, intra- and inter-laboratory, with exclusion of human errors connected with the above described presently used procedures.

I claim:

1. A kit for use in the determination of the proliferative activity of a human tumor consisting essentially of a first vial which contains in lyophilized form McCoy's 5A culture medium, 190 U.I. of penicillin, 190 ug of streptomycin, fetal calf serum and a radioactive metabolic precursor, which is 3H-thymidine, a second vial containing distilled water, a third vial which contains a fixative agent, a fourth vial which contains ethyl alcohol, a container for waste liquids and means for the aspiration and transfer of said liquids.

2. The kit according to claim 1, wherein the volume of said culture medium, said antibiotic, said serum and said radioactive metabolic precursor in said vial (a) is about 2 cc.

3. The kit according to claim 1, wherein the volume of distilled water in said vial (b) ranges from about 0.6 to about 2 cc.

4. A method of obtaining a stabilized specimen containing tumoral tissue for determination of the tumor proliferative activity, which consists of providing a kit consisting essentially of a first vial which contains in lyophilized form McCoy's 5A culture medium, 190 U.I. of penicillin, 190 ug of streptomycin, fetal calf serum and a radioactive metabolic precursor, which is 3H-thymidine, a second vial containing distilled water, a third vial which contains a fixative agent, a fourth vial which contains ethyl alcohol, a container for waste liquids and means for the aspiration and transfer of said liquids, adding the distilled water from said second vial to the lyophilized product in said first vial, after one hour adding a sample of the tumoral tissue to said first vial, removing the liquid after a suitable time period by transfer to said container, introducing the fixative agent from said third vial into said first vial, removing liquid after a suitable time period, introducing ethyl alcohol from said fourth vial into said first vial whereby a stabilized test specimen is obtained and measuring the labeling index by the autoradiographic method.

* * * * *